United States Patent [19]

Cawse et al.

[11] 4,111,975
[45] Sep. 5, 1978

[54] CATALYTIC PROCESS FOR PRODUCING POLYHYDRIC ALCOHOLS AND DERIVATIVES

[75] Inventors: James Norman Cawse; Jose Luis Vidal, both of Charleston, W. Va.

[73] Assignee: Union Carbide Corporation, New York, N.Y.

[21] Appl. No.: 782,986

[22] Filed: Mar. 30, 1977

[51] Int. Cl.$^2$ ............................................. C07C 27/06
[52] U.S. Cl. ........................... 260/449 L; 260/449 R; 260/449.5; 252/431 R; 252/431 N; 252/431 L; 252/431 P; 252/443; 560/231
[58] Field of Search ..................... 260/449 R, 449 L

[56] References Cited

U.S. PATENT DOCUMENTS

| | | | |
|---|---|---|---|
| 3,833,634 | 9/1974 | Pruett et al. ..................... | 260/449 R |
| 3,888,877 | 6/1975 | Lehn ............................... | 260/327 R |
| 3,952,039 | 4/1976 | Walker et al. ..................... | 260/449 |
| 3,957,857 | 5/1976 | Pruett et al. ..................... | 260/449 R |

OTHER PUBLICATIONS

Christensen et al., Chem. Rev. (1974), vol. 74, No. 3, pp. 351–371.
"Kryptofix", E. M. Laboratories Inc., Elmsford, N. Y. 10523.

*Primary Examiner*—Howard T. Mars
*Attorney, Agent, or Firm*—Bernard Lieberman

[57] ABSTRACT

A process for producing polyhydric alcohols, their ether and ester derivatives, oligomers of such alcohols and monohydric alcohols and their ester derivatives by reacting hydrogen and oxides of carbon in the presence of a rhodium carbonyl complex, an alkali metal cation and a cryptand.

11 Claims, 1 Drawing Figure

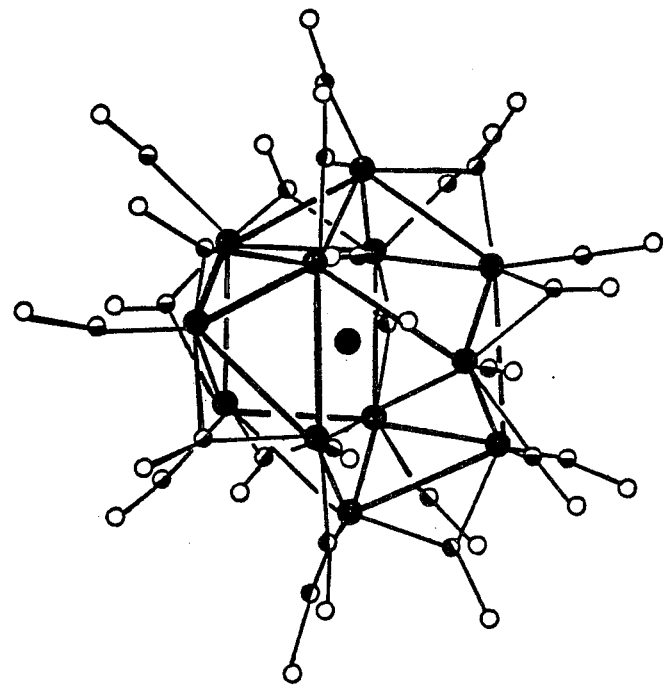
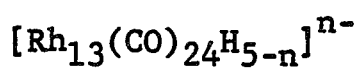
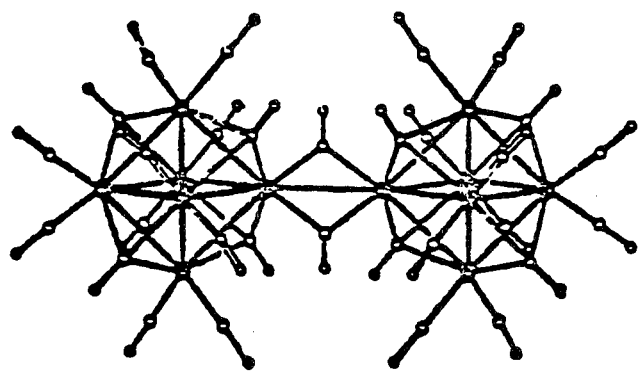
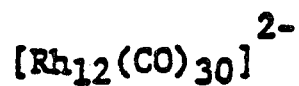

CATALYTIC PROCESS FOR PRODUCING POLYHYDRIC ALCOHOLS AND DERIVATIVES

CROSS-REFERENCE TO RELATED APPLICATION

This application is related to copending U.S. application Ser. No. 727,646, filed on Sept. 29, 1976 which is directed to the use of novel solvents, such as cryptands, in a process for producing alkane polyols from mixtures of carbon monoxide and hydrogen in the presence of a rhodium carbonyl complex catalyst.

This invention relates to the production of polyhydric alcohols, their ether and ester derivatives, and oligomers of such alcohols. This invention also produces monohydric alcohols such as methanol and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the furture. The consequence of this has been the recognition of the need for a new low cost source of chemicals which can be converted into such polyhydric alcohols.

This invention is directed to the process of making alkane diols and triols, containing 2, 3 or 4 carbon atoms, and derivatives such as their esters. Key products of the process of this invention are ethylene glycol and its ester derivatives. Byproducts of this invention are the lesser valuable, but valuable nevertheless, monohydric alkanols such as methanol, ethanol and propanols, and their ether and ester derivatives. The products of the process of this invention contain carbon, hydrogen and oxygen.

There are described in U.S. Pat. No. 3,833,634, issued Sept. 3, 1974, and U.S. Pat. No. 3,957,857, issued May 18, 1976, processes for reacting hydrogen and oxides of carbon in the presence of rhodium carbonyl complex catalysts. U.S. Pat. No. 3,957,857 is concerned with a rhodium carbonyl complex which is a rhodium carbonyl cluster exhibiting a particular infrared spectrum. The conditions, broadly speaking, employed in those processes involve reacting a mixture of an oxide of carbon and hydrogen with a catalytic amount of rhodium in complex combination with carbon monoxide, at a temperature of between about 100° C to about 375° C and a pressure of between about 500 p.s.i.a. to about 50,000 p.s.i.a. As described in these patents, the process is carried out in a homogeneous liquid phase mixture in the presence of one or more ligands selected from among groups referred to in the patent, as organic oxygen ligands, organic nitrogen ligands and organic azaoxa ligands. In addition to the aforementioned U.S. Patents, the following U.S. Patents and U.S. Patent applications amplify the development of the processes for making alkane polyols from mixtures of hydrogen and oxides of carbon:

| U.S.P. 3,878,292 | Patented April 15, 1975 |
| U.S.P. 3,878,290 | Patented April 15, 1975 |
| U.S.P. 3,878,214 | Patented April 15, 1975 |
| U.S.P. 3,886,364 | Patented May 27, 1975 |
| U.S.P. 3,940,432 | Patented February 24, 1976 |
| U.S.P. 3,929,969 | Patented December 30, 1975 |
| U.S.P. 3,952,039 | Patented April 20, 1976 |
| U.S.P. 3,948,965 | Patented April 6, 1976 |
| U.S.P. 3,944,588 | Patented March 16, 1976 |
| U.S.Ser. No. 455,380 | Filed March 27, 1974 |
| U.S.Ser. No. 455,379 | Filed March 27, 1974 |
| U.S.Ser. No. 526,942 | Filed November 25, 1974 |
| U.S.Ser. No. 488,139 | Filed July 12, 1974 |
| U.S.Ser. No. 488,140 | Filed July 12, 1974 |
| U.S.Ser. No. 506,862 | Filed September 17, 1974 |
| U.S.Ser. No. 506,864 | Filed September 17, 1974 |
| U.S.Ser. No. 506,865 | Filed September 17, 1974 |
| U.S.Ser. No. 511,740 | Filed October 3, 1974 |
| U.S.Ser. No. 615,093 | Filed September 19, 1975 |
| U.S.Ser. No. 537,885 | Filed January 2, 1975 |
| U.S.Ser. No. 618,023 | Filed September 30, 1975 |
| U.S.Ser. No. 618,061 | Filed September 30, 1975 |
| U.S.Ser. No. 618,021 | Filed September 30, 1975 |
| U.S.Ser. No. 727,646 | Filed September 29, 1976 |

This invention constitutes an addition to or an improvement of the inventions of the foregoing patents and patent applications.

U.S. Pat. No. 3,952,039 issued Apr. 20, 1976, describes the use of alkali metal cations to improve the yield of the desired alkane diols and triols of the invention. The most preferred operating temperatures disclosed for this process are below about 240° C due to the fact that some signs of rhodium catalyst instability are noted at more elevated temperatures, particularly in a solvent such as tetraglyme. The effect of such instability is a decline in catalyst performance and efficiency. From the viewpoint of reaction kinetics, higher operating temperatures are desirable insofar as the production rates of methanol, ethylene glycol and other oxygenated organic compounds vary directly with temperature; the higher the temperature, the greater the productivity. Consequently, stabilization of the rhodium catalyst during high-temperature operation is particularly advantageous for obtaining higher rates of product formation.

It has been found that the use of a macrocyclic diaza compound in accordance with the invention, such compound being of the type commonly referred to as a cryptand, in combination with an alkali metal cation in a homogeneous liquid phase mixture containing a catalytic amount of rhodium carbonyl complex results in enhanced rates of formation of alkane polyols from a reaction mixture of hydrogen and oxides of carbon. That is, the complex combination of alkali metal cation with a cryptand has been found to enhance the production of polyols in accordance with the invention relative to their production in the absence of such cryptand, or optionally in the presence of an amine promoter in lieu of such cryptand. The reaction temperature is from about 100° C to about 450° C and at a pressure of about 500 p.s.i.a. to about 50,000 p.s.i.a. sufficient to produce the alkane polyol. At temperatures of 240° C and above the rates of polyol formation are particularly enhanced.

Although the exact mechanism by which cryptands are capable of providing the above-described enhanced production rates of polyols from synthesis gas is not fully understood, it is nevertheless believed to be due to the cation complexing properties of cryptands to form cryptates. It has been postulated that the rhodium carbonyl complex is present in the organic solvent in the form of an anion. Altering the affinity of such anion with the cations in the solvent is believed to affect the retention of rhodium in the homogeneous liquid phase mixture. Thus, the formation of a cation-containing macrocyclic complex in accordance with the invention is believed to weaken the ion pairing of anions and cations and thereby enhance the stability of the rhodium catalyst in solution.

The term "oxides of carbon" as used throughout the specification and claims is intended to mean carbon monoxide and mixtures of carbon monoxide and carbon dioxide either introduced as such or formed in the reaction.

The cryptands of the present invention have been extensively characterized in the prior art literature. The term "cryptand" as used throughout the specification and claims refers to those compounds defined in U.S. Pat. No. 3,888,877 to Lehn as comprising a hetero-macrocyclic compound having nitrogen bridgehead atoms separated by at least two, and preferably three, hydrocarbon bridges, each bridge having at least 3 adjoining atoms, at least one of said bridges having hydrocarbon radicals separated at intervals by hetero-substitutents of the group consisting of oxygen, sulphur, and amino, there being at least two hetero substitutents in said macrocyclic nucleus in addition to the nitrogen bridgehead atoms, and when said macrocyclic nucleus is a monocyclic structure, of said two hetero substitutents, one is either oxygen or sulphur and the other is either oxygen or amino.

Some significant publications wherein cryptands has been depicted and characterized in detail include:

(1) U.S. Pat. No. 3,888,877 to Lehn, issued June 10, 1975;

(2) "Structure and Bonding", vol. 16, (1973) published by Springer-Verlang, New York, N.Y.; Chapter 4 entitled "Complexes of Alkali and Alkaline Earth Metal Cations With Synthetic Organic Ligands", pp. 37–63, is particularly relevant; and (3) Christensen et al., *Chemical Reviews*, vol. 74, No. 3, pp. 351–384 (1974).

Bicyclic cryptands (i.e., those having three bridging chains) are among the preferred macrocyclic diaza compounds of the invention. Monocyclic compounds (i.e., those having two bridging chains) are also suitable, albeit less effective. Polycyclic cryptands having more than three bridging chains such as compound No. 16 shown below are particularly preferred for purposes of the invention.

The structural formula, chemical name and abbreviated name (where available) of some preferred cryptands of the present invention are shown below:

| | Formula | Chemical Name | Abbreviated Name |
|---|---|---|---|
| 1. | | 4,7,13,18-tetraoxa-1, 10-diazabicyclohexacosane | [2.1.1] |
| 2. | | 4,7,13,16,21-pentaoxa-1, 10-diazabicyclo-tricosane | [2.2.1] |
| 3. | | 4,7,13,16,21,24,-hexaoxa-1, 10-diazabicyclo pentatriacontane | [2.2.2] |
| 4. | | 4,7,10,16,19,24,27,-heptaoxa-1, 13-diazabicyclo nonacosane | [3.2.2] |
| 5. | | 4,7,10,16,19,22,27,30,-octaoxa-1, 13-diazabicyclo dotriacontane | [3.3.2] |
| 6. | | 4,7,13,16-tetraoxa-1, 10-diazabicyclohexacosane | |
| 7. | | 4,7,13,16-tetraoxa-21,24-dithia-1, 10-diazabicyclo hexacosane | |

| | Formula | Chemical Name | Abbreviated Name |
|---|---|---|---|
| 8. | 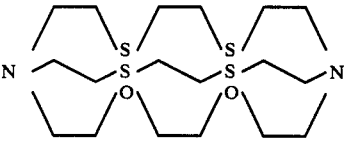 | 4,7-dioxa-13,16,21,24-tetrathia-1,10-dizabicyclo hexacosane | |
| 9. | 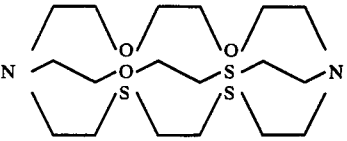 | 4,13,16-trioxa-7,21,24-trithia-1,10-diazabicyclo hexacosane | |
| 10. | 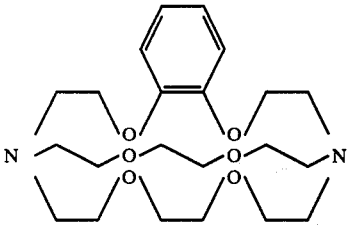 | 4,11,17,20,25,28-hexaoxa-1,14-diazatricyclo-triaconta-5,7,9-triene | [2B.2.2] |
| 11. | 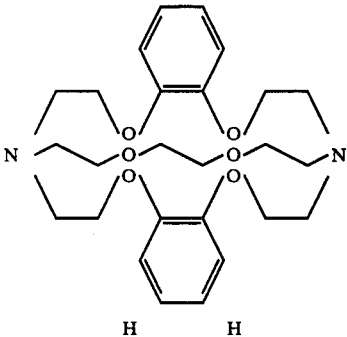 | 4,11,17,24,29,32-hexaoxa-1,14-dizatetracyclo-tetratriaconta-5,7,9,18,20,22-hexane | [2B.2B.2] |
| 12. | 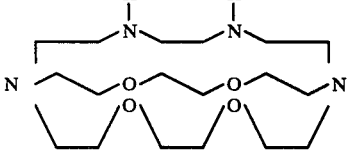 | 4,7,13,16-tetraoxa-1,10,21,24-tetraazabicyclo[8.8.8]hexacosane | |
| 13. | 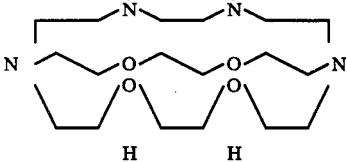 | 21,24-dimethyl-4,7,13,16-tetraoxa-1,10,21,24-tetraazabicyclo hexacosane | |
| 14 | 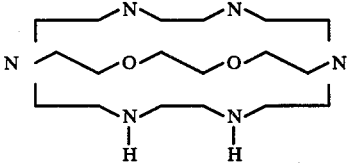 | 4,7-dioxa-1,10,13,16,21,24-hexaazabicyclo-hexacosane | |
| 15 | 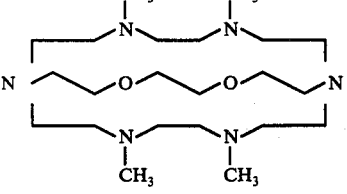 | 13,16,21,24-tetramethyl-4,7-dioxa-1,10,13,16,21,24-hexaaza bicyclo hexacosane | |

| Formula | Chemical Name | Abbreviated Name |
|---|---|---|
| 16  | Refer to description of compound in Graf and Lehn, J.Amer. Chem. Soc. 97, p 5022 (1975) | |

The metal cation may be conveniently provided to the reaction mixture in the form of its alkali metal salt. Suitable alkali metal salts useful in the present invention include the alkali metal halides, for instance the fluoride, chloride, bromide and iodide salts and the alkali metal carboxylates, such as formate, acetate, propionate, and butyrate salts. Other alkali metal salts useful in the present invention include compounds of the general formula:

$$M-O-R$$

wherein M is an alkali metal selected from the group of sodium, potassium, lithium, rubidium, and cesium and R can represent hydrogen; an alkyl group, such as methyl, ethyl, isopropyl, 2-ethylhexyl and the like; or an aryl group such as phenyl, tolyl, napthyl, and the like; or a functionally substituted alkyl such as ethoxymethyl, ethoxyethyl, phenoxyethyl, and the like, or a cyclic or bicyclic hydrocarbon such as cyclohexyl, cyclopentyl, bicycloheptyl and the like; or a heterocyclic group, such as pyridinyl, quinolinyl, and the like.

The preferred alkali metal salts useful in the present invention are the formate, acetate, benzoate and fluoride salts of potassium and cesium.

The molar ratio of cryptand to alkali metal ion may vary from about 1:1 to about 200:1 depending upon the reaction temperature. At temperatures of about 200° C, molar ratios as low as 1:1, and even lower, may be suitable for the reaction while at more elevated temperatures, such as, 280° C and above, molar ratios of 200:1 may be necessary for most effective operation. At a temperature of from about 220° C–280° C, the preferred cryptand to alkali metal ion ratio is generally within the range of from about 1:1 to 60:1. While the rate of polyol formation is particularly enhanced at temperatures of about 240° C and above, the decomposition of cryptands at such temperatures may be significant.

Potassium — [3.2.2] and cesium — [3.2.2] are among the most preferred alkali metal cation - cryptand complexes for the practice of the present invention.

A normally liquid organic solvent is employed in an amount sufficient to maintain a homogeneous reaction mixture containing rhodium carbonyl cluster, the cryptand and the alkali metal cation. The solvents which are generally suitable for the practice of the present invention include, for example, saturated and aromatic hydrocarbons, e.g., hexane, octane, dodecane, naptha, decalin, tetrahydronaphthalene, kerosene, mineral oil, cyclohexane, cycloheptane, alkylcycloalkane, benzene, toluene, xylene, naphthalene, alkylnaphthalene, etc; ethers such as tetrahydrofuran, tetrahydropyran, diethyl ether, 1,2-dimethoxybenzene, 1,2-ethoxybenzene, the mono- and dialkyl ethers of alkylene glycols and polyalkylene glycols, such as ethylene glycol, or propylene glycol, of butylene glycol, of diethylene glycol, of dipropylene glycol, of triethylene glycol, of tetraethylene glycol of pentaethylene glycol, of dibutylene glycol, of oxyethyleneoxypropylene glycol, etc., preferably, those in which the alkylene group contains 2 carbon atoms in the divalent moeity, such as, ethylene and 1,2-propylene; carboxylic acids such as acetic acid, propionic acid, butyric acid, caproic acid, stearic acid, benzoic acid, cyclohexanecarboxylic acid, etc; alkanols such as methanol, ethanol, propanol, isobutanol, 2-ethyl-hexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water, anhydrides such as phthalic anhydride, acetic anhydride, etc.; and lactones such as γ-butyrolactone and valerolactone, etc.

The mono and dialkylethers of triethylene and tetraethylene glycol are among the preferred solvents in the practice of the present invention.

The preferred solvent for the practice of the present invention is tetraglyme (the dimethylether of tetraethylene glycol). Sulfolane and tetraglyme-sulfolane mixtures may also be used for the invention although they are generally less effective above temperatures of about 220° C. The term "sulfolane" as used herein refers to tetramethylene sulfone and substituted tetramethylene sulfone.

The alkali metal cation is preferably present in the reaction mixture in a concentration of from about 0.5 to 2.0 moles of cation per six atoms of rhodium charged to the reactor. The range of 1 to 2.0 moles of cation per six atoms of rhodium is particularly preferred.

The rhodium carbonyl complexes suitable for use in the present invention may be in the form of rhodium carbonyl clusters. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster". The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C—O), in which the carbonyl may be "terminal", "edge-bridging", and/or "face-bridging". They may also contain hydrogen and carbon in forms other than carbonyl.

The following are illustrative of what is believed to be the structure of two distinct rhodium carbonyl clusters and both are suitable for use in this invention, as further illustrated in the drawings.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp299–302, June (1969). Of particular analytical utility in the present invention is the use of infrared spectroscopy which allows for characterization of the particular rhodium carbonyl complex present during the operation of the process of the invention.

A particularly desirable infrared cell construction is described in U.S. Pat. No. 3,886,364, issued May 27, 1975 and its disclosure of a preferred cell construction is incorporated herein by reference.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. Depending on various factors such as the promoter of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable in the practice of the invention.

The novel process is suitably effected over a wide superatmospheric pressure range of from about 500 psia to about 50,000 psia. Pressures as high as 50,000 psia, and higher can be employed but with no apparent advantages attendant thereto which offset the unattractive plant investment outlay required for such high pressure equipment.

In one embodiment of this invention the upper pressure limitation is approximately 16,000 psia. Effecting the present process below about 16,000 psia, especially below about 13,000 psia, and preferably at pressures below about 8000 psia, results in cost advantages which are associated with low pressure equipment requirements. A suitable pressure range for effecting the reaction is from about 1000 psia to about 16,000 psia, preferably from about 4000 to about 16,000 psia.

In a preferred embodiment of the present invention the pressures referred to above represent the total pressures of hydrogen and oxides of carbon in the reactor.

The operative temperature which may be employed can vary over a wide range of elevated temperatures. In general, the novel process can be conducted at a temperature in the range of from about 100° C. and upwards to approximately 375° C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

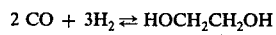

$$2\ CO + 3H_2 \rightleftarrows HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150° C. to about 320° C., and desirably from about 210° C. to about 280° C.

The novel process is effective for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or solvents, can be recycled to the reaction zone, if desired. All or a portion of such fraction can be removed for recovery of the rhodium values or regeneration to the active catalyst and can be intermittently added to the recycle stream or directly to the reaction zone.

The active forms of the rhodium carbonyl clusters may be prepared by various techniques. They can be performed and then introduced into the reaction zone. Alternatively, any of the host of rhodium-containing substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium(II) propionate, rhodium(II) butyrate, rhodium(II) valerate, rhodium(III) naphthenate, rhodium dicarbonyl acetylacetonate, rhodium tri(acetylacetonate), rhodium trihydroxide, indenyl-rhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the solvent mixture. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the solvent mixture is catalytically active in this process.

The reaction of the present invention is conducted in what is believed to be a homogeneous liquid phase, which means that the catalyst, the reaction products and the promoter if present are in solution. Though the reaction to produce alcohols is essentially homogeneous, there may be small amounts of insoluble catalyst particles depending on the reaction conditions employed.

In the examples below as set forth in the Tables below, the following procedure was employed:

A 150 ml. capacity stainless steel reactor capable of withstanding pressures up to 7,000 atmospheres was charged with a premix of 75 cubic centimeters (cc) of a specified solvent, a specified amount of rhodium in the form of rhodium dicarbonylacetylacetonate, and specified amounts of one or more of an alkali metal salt (where indicated), an amine promoter (where indicated) and salt promoter (where indicated). The reactor was sealed and charged with a gaseous mixture containing equal molar amounts of carbon monoxide and hydrogen to a pressure as specified below. Heat was applied to the reactor and its contents; when the temperature of the mixture inside the reactor reached 190° C, as measured by a suitably placed thermocouple, an additional adjustment of carbon monoxide and hydrogen ($H_2$:CO=1:1 mole ratio) was made to bring the pressure back to that which is specified in the Tables. The temperatures and pressures were maintained as indicated in the Tables.

After the reaction was terminated, the vessel and its contents were cooled to room temperature, the excess gas vented and the reaction product mixture was removed. Analysis of the reaction product mixture was made by gas chromatographic analysis using a Hewlett Packard FM$^{TM}$ model 810 Research Chromatograph.

The rate of production of ethylene glycol and methanol as determined from the analysis of the product mixture is shown in the Tables, as well as the rhodium discovery based on the total rhodium charged to the reactor.

Rhodium recovery was determined by atomic absorption analysis of the contents of the reactor after the venting of the unreacted gases at the end of the reaction. Atomic absorption analysis was run using a Perkin and Elmer Model 303 Atomic Absorption Spectrophotometer. The rhodium recovery values may be characterized as the percent rhodium based on the total rhodium charged to the reactor that is soluble or suspended in the reaction mixture after the specified reaction time.

TABLE I

COMPARISON OF ALKALI METAL SALT-CRYPTAND MIXTURES IN TETRAGLYME WITH CATALYST SYSTEMS USING SALT PROMOTERS AND/OR AMINES IN TETRAGLYME, SULFOLANE AND TETRAGLYME-SULFOLANE SOLVENTS

| Ex. | Salt (mmoles) | Amine (mmoles) | [Cryptand] mmoles | T° C | P(psig) | Solvent | Rate(Mole . Liter$^{-1}$Hour$^{-1}$) $CH_3OH$ | $HOCH_2CH_2OH$ | % Rh Recovered In Solution |
|---|---|---|---|---|---|---|---|---|---|
| 1 | $CsC_6H_5CO_2$, (0.65) | $NC_6H_{15}O_3$, (8.0) | — | 240 | 8000 | Tetraglyme | 0.32 | 0.26 | 36 |
| 2 | $[(C_6H_5)_3P]_2NCH_3CO_2$, (0.75) | $C_5H_5N$, (1.25) | — | 240 | " | " | 0.28 | 0.35 | 81 |
| 3 | $K CH_3CO_2$, (0.75) | — | [2.2.2], 4.0 | 240 | " | " | 0.38 | 0.38 | 79 |
| 4 | $CsC_6H_5CO_2$, (0.62) | — | [3.2.2], 12.0 | 250 | " | " | 0.59 | 0.52 | 78 |
| 5 | $CsC_6H_5CO_2$, (0.62) | — | — | 250 | " | " | 0.09 | 0.04 | 68 |
| 6 | $CsPCH_3SO_4C_6H_4CO_2$, (0.65) | — | — | 250 | " | Sulfolane | 0.40 | 0.36 | 78 |
| 7 | $NH_4CH_3COO$, (0.75) | — | — | 240 | " | " | 0.30 | 0.24 | 83 |
| 8 | — | $C_5H_{11}ON$, (5.0) | — | 250 | " | " | 0.38 | 0.35 | 70 |
| 9 | $CsC_6H_5CO_2$, (0.65) | $C_5H_{11}ON$, (5.0) | — | 250 | " | " | 0.57 | 0.34 | 76 |
| 10 | $CsHCO_2$, (0.65) | $C_9H_{24}O_3NB$, (2.5) | — | 260 | " | " | 0.68 | 0.34 | 79 |
| 11 | $KCH_3CO_2$, (0.75) | — | [2.2.2], 40.0 | 260 | " | Tetraglyme | 0.56 | 0.44 | 66 |
| 12 | $KCH_3CO_2$, (0.75) | $C_5H_5N$, (1.25) | — | 260 | " | " | 0.15 | 0.02 | 2. |
| 13 | $CsC_6H_5CO_2$, (0.75) | $C_5H_5N$, (1.25) | — | 260 | 12500 | Tetraglyme/$^a$ Sulfolane | 2.94 | 2.74 | 98 |
| 14 | $CsC_6H_5CO_2$, (0.75) | — | — | 260 | " | " | 2.69 | 2.43 | |
| 15 | $KCH_3CO_2$, (0.75) | — | [2,2,2], 32.0 | 270 | " | Tetraglyme | 3.4 | 3.96 | 72 |
| 16 | $KCH_3CO_2$, (0.90) | — | [2.2.2], 32.0 | 270 | " | " | 4.04 | 4.54 | 72 |
| 17 | $CsC_6H_5CO_2$, (0.75) | — | [3.2.2], 12.0 | 260 | " | " | 1.98 | 2.80 | 97 |
| 18 | $KCH_3CO_2$, (0.90) | — | — | 270 | " | " | 0.31 | 0.02 | 3. |
| 19 | $KCH_3CO_2$, (0.95) | $C_5H_5N$, (1.25) | — | 270 | " | " | 0.47 | 0.12 | 3. |

Data for all runs at $H_2/CO = 1$, 4 hours, 75 cc solvent and 3.0 mmoles Rh (CO)$_2$ acac.
Data for Examples 11, 15, 16 and 17 has been linearly extrapolated from 1.5 mmoles of catalyst to 3.0 mmoles Rh(CO)$_2$ acac for purposes of comparison.
$^a$Tetraglyme/sulfolane is 50-50 volume % mixture.

TABLE II

COMPARISON OF ALKALI METAL ACETATES AND ALKALI METAL ACETATE-CRYPTAND MIXTURES IN TETRAGLYME

| Examples | $MCH_3COO^1$ (mmoles) | [Cryptand]mmoles | T° C | Rate(Mole . Liter$^{-1}$Hour$^{-1}$) $CH_3OH$ | $HOCH_2CH_2OH$ | % Soluble Rh Recovered |
|---|---|---|---|---|---|---|
| 20 | $LiCH_3COO$ (0.75) | — | 240 | 0.4 | 0 | 2 |
| 21 | " | [2.1.1], 1.0 | " | 0.132 | 0.101 | 8 |
| 22 | " | [2.1.1], 4.0 | " | 0.290 | 0.232 | 23 |
| 23 | $NaCH_3COO$ (0.75) | — | " | 0.041 | 0.01 | 2 |
| 24 | " | [2.2.1], 4.0 | " | 0.231 | 0.248 | 29 |
| 25 | " | [2.2.1], 8.0 | " | 0.309 | 0.241 | 29 |
| 26 | $KCH_3COO$ (0.75) | — | " | 0.149 | 0.078 | 8 |
| 27 | " | [2.2.2], 4.0 | " | 0.380 | 0.377 | 79 |
| 28 | " | [2.2.2], 6.0 | " | 0.383 | 0.343 | 59 |
| 29 | $RbCH_3COO$ (0.85) | — | 220 | 0.077 | 0.063 | 45 |
| 30 | " | [2.2.2], 1.00 | " | 0.237 | 0.225 | 79 |
| 31 | " | [2.2.2], 1.25 | " | 0.227 | 0.209 | 78 |

$^1MCH_3COO$ represents the alkali acetate co-promoters.
All runs at $H_2/CO = 1$,800 psig, 4 hours, 30 mmoles Rh (CO)$_2$ acac and 75 cc tetraglyme solvent.

TABLE III

COMPARISON OF $KCH_3COO$-AMINE MIXTURES AND $KCH_3COO$-[2.2.2] IN TETRAGLYME

| Example | m moles of $KCH_3COO$ | Amine, (m moles) | m moles of [2.2.2] | T° - C | Rate Mole liter$^{-1}$(hour$^{-1}$) $CH_3OH$ | $HOCH_2CH_2OH$ | % Soluble Rh Recovery |
|---|---|---|---|---|---|---|---|
| 32 | 0.75 | $N(CH_2CH_2OH)_3$, (0.75) | — | 220 | 0.061 | 0.064 | 6 |
| 33 | 0.75 | $N(CH_2CH_2OH)_3$, (1.50) | — | " | 0.067 | 0.102 | 7 |
| 34 | 0.75 | $C_5H_5N$. (1.25) | — | " | 0.040 | 0.037 | 7 |
| 35 | 0.75 | $N(CH_2CH_2OH)_3$, (8.0) | — | " | 0.151 | 0.144 | 30 |
| 36 | 0.75 | $N(CH_2CH_2OH)_3$, (8.0) | — | 240 | 0.245 | 0.156 | 6 |
| 37 | 0.75 | $N(CH_2CH_2OH)_3$, (20.0) | — | " | 0.175 | 0.130 | 10 |
| 38 | 0.75 | — | 1.00 | 220 | 0.156 | 0.207 | 75 |
| 39 | 0.75 | — | 1.25 | " | 0.214 | 0.292 | 82 |
| 40 | 0.75 | — | 4.00 | 240 | 0.380 | 0.377 | 79 |
| 41 | 0.75 | — | 6.00 | " | 0.383 | 0.343 | 60 |
| 42 | — | — | 0.75 | 220 | 0.16 | 0.055 | 59 |

All runs at $H_2/CO = 1$. 8000 psig, 4 hours, 3.0 m moles Rh(CO)$_2$acac and 75 cc tetraglyme solvent

TABLE IV $KCH_3COO$—[2.2.2] MIXTURES IN TETRAGLYME

| Examples | mmoles of Rh(CO)$_2$ acac | mmoles of $KCH_3COO$ | mmoles of [2.2.2] | T° C | P(psig) | Rate (mole.Liter$^{-1}$Hour$^{-1}$) $CH_3OH$ | $HOCH_2CH_2OH$ | % Soluble Rh Recovered |
|---|---|---|---|---|---|---|---|---|
| 43 | 3.0 | 0.75 | 0.25 | 220 | 8000 | 0.150 | 0.540 | 38 |
| 44 | " | " | 0.50 | " | " | 0.201 | 0.178 | 76 |
| 45 | " | " | 0.57 | " | " | 0.134 | 0.202 | 82 |
| 46 | " | " | 1.00 | " | " | 0.156 | 0.207 | 75 |
| 47 | " | " | 1.25 | " | " | 0.214 | 0.920 | 82 |
| 48 | " | " | 0.75 | 240 | " | 0.210 | 0.240 | 18 |
| 49 | " | " | 0.98 | " | " | 0.219 | 0.291 | 36 |

TABLE IV-continued

KCH₃COO—[2.2.2] MIXTURES IN TETRAGLYME

| Examples | mmoles of Rh(CO)₂ acac | mmoles of KCH₃COO | mmoles of [2.2.2] | T° C | P(psig) | Rate (mole.Liter⁻¹Hour⁻¹) CH₃OH | HOCH₂CH₂OH | % Soluble Rh Recovered |
|---|---|---|---|---|---|---|---|---|
| 50 | " | " | 1.25 | " | " | 0.244 | 0.267 | 37 |
| 51 | " | " | 1.50 | " | " | 0.240 | 0.302 | 43 |
| 52 | " | " | 2.00 | " | " | 0.328 | 0.310 | 79 |
| 53 | " | " | 4.00 | " | " | 0.380 | 0.377 | 59 |
| 54 | " | " | 6.00 | " | " | 0.383 | 0.343 | 50 |
| 55 | " | " | 10.00 | " | " | 0.228 | 0.376 | |
| 56 | " | " | 40.00 | 260 | " | 0.465 | 0.440 | 33 |
| 57 | 1.5 | 0.375 | 2.00 | 240 | 12500 | 0.42 | 0.76 | 81 |
| 58 | " | " | 4.00 | 250 | " | 0.81 | 1.13 | 81 |
| 59 | 1.5 | 0.375 | 4.00 | 260 | 12500 | 1.17 | 1.20 | 54 |
| 60 | 1.5 | " | 8.00 | " | " | 0.91 | 1.32 | 73 |
| 61 | 1.5 | 0.300 | 16.00 | 270 | " | 1.61 | 1.61 | 66 |
| 62 | 1.5 | 0.375 | 16.00 | " | " | 1.71 | 1.98 | 72 |
| 63 | 1.5 | 0.450 | 16.00 | " | " | 2.02 | 2.27 | 72 |
| 64 | 1.5 | 0.525 | 16.00 | " | " | 2.12 | 1.99 | |
| 65 | 1.5 | 0.600 | 16.00 | " | " | 1.76 | 1.79 | 65 |
| 66 | 3.0 | 0.75 | 1.00 | 220 | 8000 | 0.156 | 0.207 | 75 |
| 67 | " | " | 4.00 | 240 | " | 0.380 | 0.377 | 79 |
| 68 | 1.5 | " | 8.00 | 260 | " | 0.91 | 1.32 | 73 |
| 69 | 1.5 | " | 16.00 | 270 | " | 2.02 | 2.27 | 72 |

All runs at H₂/CO = 1, 4 hours, 75cc tetraglyme solvent.

What is claimed is:

1. A process for producing alkane polyols in a homogeneous liquid phase mixture which comprises reacting at a temperature of from about 100° C to about 375° C and a pressure of from about 500 psia to about 50,000 psia, a mixture comprising oxides of carbon and hydrogen in the presence of a rhodium carbonyl complex and as promoters an alkali metal cation and a cryptand.

2. The process of claim 1 wherein the temperature is from about 150° C to about 320° C.

3. The process of claim 1 wherein the temperature is from about 210° C to about 280° C.

4. The process of claim 1 wherein the reaction is effected in the presence of an organic solvent.

5. The process of claim 4 wherein the solvent is tetraglyme.

6. The process of claim 1 wherein the cryptand is 4, 7, 13, 16, 21 24-hexaoxa-1, 10-diazabicyclopentatriacontane or [2.2.2].

7. The process of claim 1 wherein the cryptand is 4, 7, 10, 16, 19, 24, 27-heptaoxa-1, 13-diazabicyclo nonacosane or [3.2.2].

8. The process of claim 1 wherein the alkali metal cation is potassium.

9. The process of claim 1 wherein the alkali metal cation is cesium.

10. The process of claim 1 wherein the molar ratio of cryptand to alkali metal cation is from about 1:1 to about 200:1.

11. The process of claim 8 wherein the temperature is within the range of from about 220° C to about 280° C and the molar ratio of cryptand to alkali metal cation is from about 1:1 to 60:1.

* * * * *

UNITED STATES PATENT AND TRADEMARK OFFICE
CERTIFICATE OF CORRECTION

PATENT NO. : 4,111,975
DATED : September 5, 1978
INVENTOR(S) : James Norman Cawse and Jose Luis Vidal It is certified that error appears in the above–identified patent and that said Letters Patent are hereby corrected as shown below:

Column 5, chemical name corresponding to Formula 11,
"4,11,17,24,29,32-hexaoxa-1,14-dizatetracyclo-tetratriaconta-5,7,9,18,20,22-hexane" should read,
--4,11,17,24,29,32-hexaoxa-1,14-diazatetracyclo-tetratriaconta-5,7,9,18,20,22-hexane--.

Signed and Sealed this

Thirtieth Day of October 1979

[SEAL]

Attest:

RUTH C. MASON
*Attesting Officer*

LUTRELLE F. PARKER
*Acting Commissioner of Patents and Trademarks*